United States Patent [19]

Burks et al.

[11] Patent Number: 5,236,901
[45] Date of Patent: Aug. 17, 1993

[54] TREATMENT FOR IRRITABLE BOWEL SYNDROME

[75] Inventors: Thomas F. Burks, Tucson, Ariz.; Cynthia A. Williams, Bellaire, Tex.

[73] Assignee: Research Corporation Technologies, Inc., Tucson, Ariz.

[21] Appl. No.: 690,490

[22] Filed: Apr. 24, 1991

Related U.S. Application Data

[63] Continuation of Ser. No. 183,857, Apr. 20, 1988, abandoned.

[51] Int. Cl.⁵ ............................................. A61K 37/02
[52] U.S. Cl. ........................................ 514/21; 514/12
[58] Field of Search ................................... 514/12, 21

[56] References Cited

PUBLICATIONS

Bost, et al. (1985) "Similarity Between the Cortictropin (ACTH) Receptor and a Peptide Encoded by an RNA that is Complementary to ACTH mRNA", *Proc. Natl. Acad. Sci., USA*, 82, 1372–1375.
Narducci, et al. (1985) "Increased Colonic Motility During Exposure to a Stressful Situation", *Digestive Diseases and Science*, 30, 40–44.
Rivier, et al. (1985) "Synthetic Competitive Antagonists of Corticotropin–Releasing Factor: Effect of ACTH Secretion in Rat", *Science*, 224, 889–891.
Rivier, et al. (1985) "Involvement of Corticptropin–Releasing Factor and Somatostatin in Stress-Induced Inhibition of Growth Hormone Secretion in the Rat", *Endocrinology*, 117, 2478–2482.
Williams, et al. (1986) "Cold Water Swim Stress Inhibits Small Intestinal Transit in Rats: No Apparent Opioid or Adrenergic Mediation", *Gastroenterology*, 90, 1800.

*Primary Examiner*—Michael G. Wityshyn
*Assistant Examiner*—Choon P. Koh
*Attorney, Agent, or Firm*—Scully, Scott, Murphy & Presser

[57] ABSTRACT

The present invention relates to a method of treatment of functional bowel disease in mammals. More specifically, this invention contemplates prophylaxis and treatment of functional bowel disease in mammals by the administration of antagonists of corticotropin releasing factor. The present invention also relates to pharmaceutical compositions of these antagonists useful in the treatment of functional bowel disease in mammals.

5 Claims, 3 Drawing Sheets

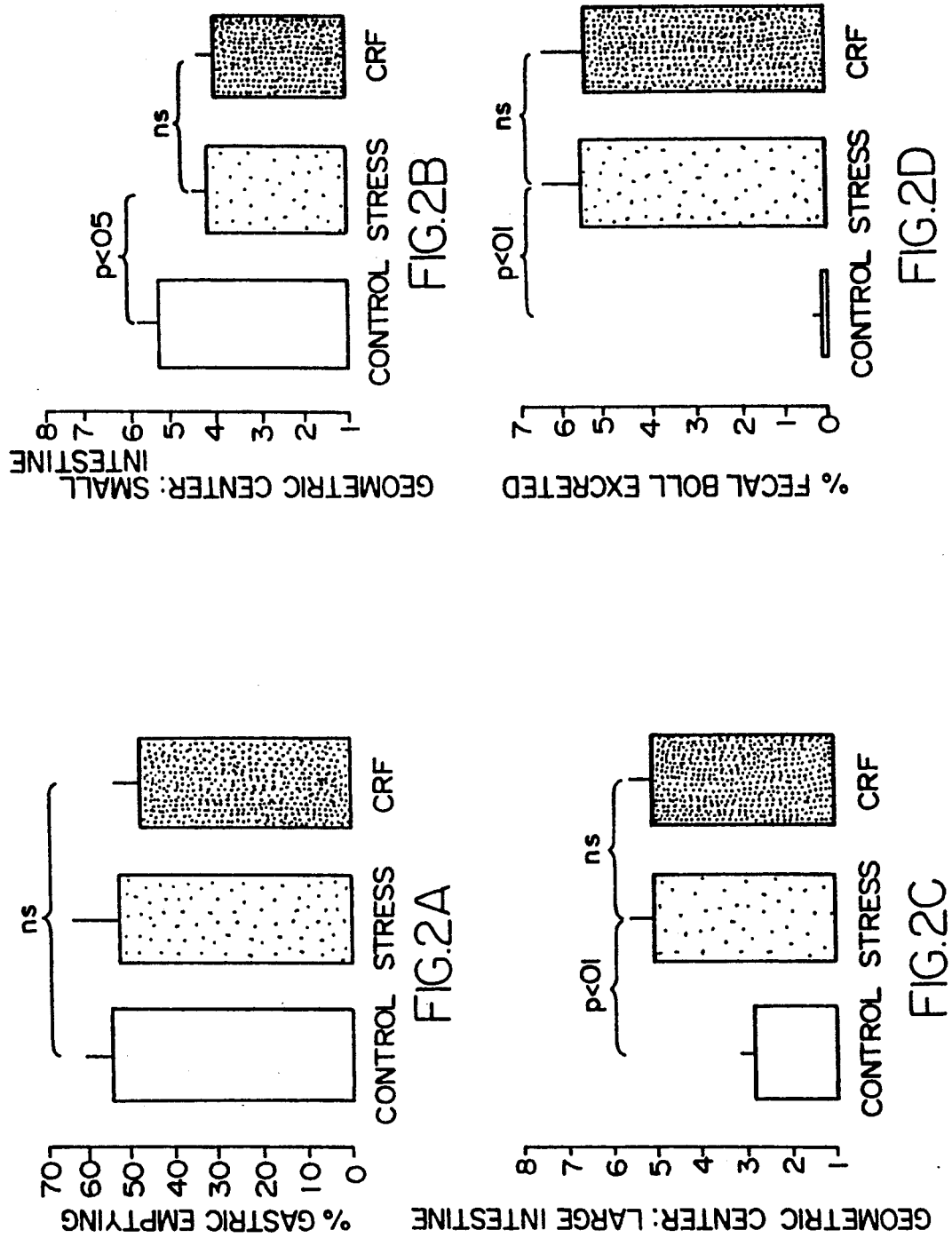

TREATMENT FOR IRRITABLE BOWEL SYNDROME

This invention was made with Government support under DA-02163 & DK-36289 awarded by the National Institutes of Health. The Government has certain rights in the invention.

This is a continuation of copending application Ser. No. 183,857, filed on Apr. 20, 1988, now abandoned.

FIELD OF THE INVENTION

The present invention relates to a method of treatment of functional bowel disease in mammals. More specifically, this invention contemplates prophylaxis and treatment of functional bowel disease in mammals by the administration of antagonists of corticotropin releasing factor. The present invention also relates to pharmaceutical compositions of these antagonists useful in the treatment of functional bowel disease in mammals.

BACKGROUND OF THE INVENTION

Stress-related functional bowel disease, including irritable bowel syndrome, irritable colon syndrome, spastic colon and irritable colon, is a common, often incapacitating gastrointestinal disorder in mammals. In humans, it is the most common chronic gastrointestinal disorder in adults and ranks equally with the common cold as the leading cause of illness-related absenteeism from the work place. Diagnosis of this disease is based on a vague symptomatology that includes abdominal pain and diarrhea, constipation, or alternating episodes of both, and treatment of the disorder is largely disappointing relative to relief and prevention of the prevailing symptoms. The etiology of intestinal dysfunction due to stress, or exacerbated by stress, is completely unknown, however, available evidence suggests that the disorder results from motility changes in the small intestine and colon brought on or exacerbated by stress.

Stress is a complex reaction that is characterized by activation of both endocrine and autonomic systems. The hypothalamic-pituitary-adrenal axis is the endocrine axis most central to the stress response, and the sympathetic nervous system, including the adrenal medulla, is the branch of the autonomic nervous system that is thought to be activated by acute stress. Corticotropin-releasing factor (CRF), a peptide comprising 41 amino acid residues and first characterized from ovine hypothalamic extracts (Vale et al., 1981, *Science Wash. DC* 213:1394–1397), is capable of activating both major systems. In addition to its role as the principal regulator of pituitary adrenocorticotropic hormone (ACTH) release (Rivier et al., 1982, *Endocrinology* 110:272–278), CRF has been shown to have a number of effects within the central nervous system: CRF elicits behavioral activation in rats (Sutton et al., 1982, *Nature Lond.* 297:331–333); stimulates the sympathoadrenomedullary pathway (Brown et al., 1982, *Endocrinology* 111:928–931); increases heart rate and blood pressure (Fisher et al., 1982, *Endocrinology* 10:2222–2224); and suppresses food consumption (Levine et al., 1983, *Neuropharmacology* 22:337–339) and sexual activity (Sirinathsinghji et al., 1983, *Nature Lond.* 305:230–235). CRF has also been shown to affect gastrointestinal function. Administered into the brain, CRF suppresses gastric acid secretion (Tache et al., 1983, *Science Wash. DC* 222:935–937), inhibits gastric emptying (Hagiwara et al. *Gastroenterology* 90:1447) and suppresses gastric and small intestinal motility (Bueno and Fioramonti, 1986, *Peptides* 7:73–77; Konturek et al., 1985, *Life Sci.* 37:1231–1240). The effects of CRF on small and large intestinal transit have not been evaluated. Because of its wide distribution within the brain and its multiple actions, which are generally associated with stress, CRF has been proposed as a "master transmitter", capable of eliciting coordinated endocrine and autonomic events characteristic of the stress response.

In accordance with the present invention, the inventors determine the role CRF plays in mediating the effects of stress on the gastrointestinal tract, by studying the actions of exogenous CRF on gastrointestinal transit using an animal model developed to study the effects of stress on intestinal motor function. As disclosed herein, the surprising discovery is made that an antagonist to CRF blocks the effects of stress on intestinal function. Accordingly, the present invention fulfils a long felt need to develop an effective treatment for stress-related functional bowel disease by the administration of effective anatagonists of CRF.

SUMMARY OF THE INVENTION

The present invention relates to the treatment of functional bowel disease.

More particularly, the invention contemplates a method of inducing regression of functional bowel disease in a mammal comprising the administration to said mammal of an effective amount of an antagonist to corticotropin-releasing factor and a pharmaceutically acceptable carrier.

In a preferred embodiment, the present invention contemplates a method of inducing regression of functional bowel disease in a human comprising the administration to said human of an effective amount of alpha-helical CRF-(9-41) and a pharmaceutically acceptable carrier.

BRIEF DESCRIPTION OF THE FIGURES

FIG. 2 is a bar diagram comparing the effects of acute wrap-restraint stress and lowest effective dose of CRF (0.3 ug i.c.v.) in rat on (A) gastric emptying; (B) small intestinal transit; (C) large intestinal transit; and (D) fecal excretion.

DETAILED DESCRIPTION OF THE INVENTION

Figure 1A:
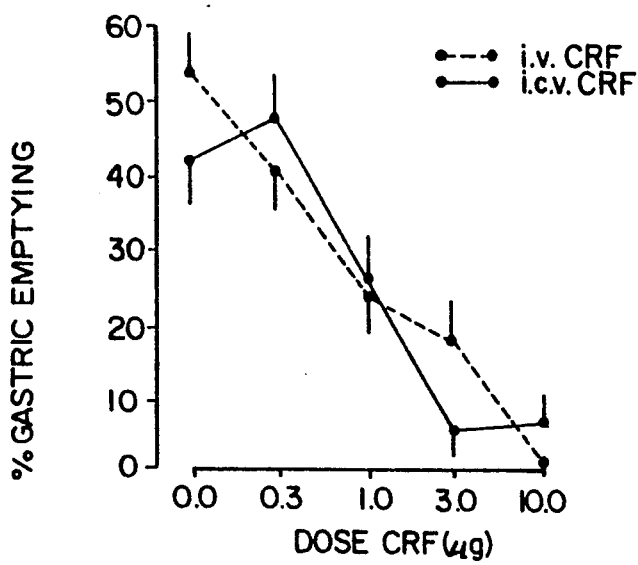
FIG. 1 is a graphical representation of the effects of exogenously administered CRF (intravenous and intracerebroventricular) on gastric emptying (graph A), small intestinal transit (graph B) and large intestinal transit (graph C).

The present invention contemplates a method of treatment of functional bowel disease in mammals comprising the administration to said mammal of an effective amount of an antagonist to corticotropin-releasing factor (CRF) and a pharmacologically acceptable carrier. By functional bowel disease, as written in the specification and claims herein, is meant to encompass all stress-related intestinal dysfunction including irritable bowel syndrome, irritable colon syndrome, spastic colon and irritable colon. In accordance with the present invention, an antagonist to CRF is defined herein to include an agent capable of interferring with the normal action of CRF. As disclosed herein, CRF is effective in altering the propulsive function of the gastrointestinal tract mimicking the effects of wrap-restraint stress on the propulsive activity of the large intestine. Accordingly, an antagonist is an agent which inhibits or reduces the action of CRF. Since CRF is involved in a wide variety of effects, in addition to the one mentioned above, within the central nervous system and outside the central nervous system, an antagonist contemplated herein is identified as an agent capable of inhibiting or reducing the effect of CRF on, for example, the stimulation of the sympatho-adrenomedullary pathway, increasing the heart rate and blood pressure and the like. Alternatively, the antagonist may selectively inhibit motor response to CRF. The antagonist of this invention may function by competing against CRF for receptor sites or may bind to, and thereby alter, the CRF molecule chemically or functionally. An example of the latter is antibodies directed to CRF. Alternatively, antibodies directed to receptor sites with binding specificity to CRF are an example of agents competing against CRF for said sites. Although many antagonists of CRF are contemplated herein, the subject invention is disclosed using one particular antagonist, i.e. alpha-helical CRF-(9-41), which, up to the present time, has been determined to be most useful in practicing this invention. This is done, however, with the understanding that the present invention encompasses all such antagonists.

Further in accordance with the present invention, treatment of functional bowel disease refers to the alleviation of symptoms relating to said disease (e.g. alternating diarrhea and constipation, and abdominal pain) by the action of an antagonist of CRF thereby preventing the response of colon to stress. Accordingly, the alleviation of symptoms, or part thereof, by affecting the cause of functional bowel disease is defined herein to be regression of said disease.

The present invention relates to antagonists of CRF, and in particular alpha-helical CRF-(9-41), useful in inducing the regression of functional bowel disease. Accordingly, the subject invention contemplates a method for inducing regression of functional bowel disease by administering a pharmaceutical composition containing an effective amount of CRF antagonist (e.g. alpha-helical CRF-(9-41)).

The active ingredients of the pharmaceutical compositions comprising said CRF antagonists exhibit excellent and effective therapeutic activity, for example, in the treatment of functional bowel disease (e.g. irritable bowel syndrome). Thus, the active ingredients of the therapeutic compositions antagonize CRF activity when administered in amounts of from about 0.5 ug to about 500 mg per kilogram of body weight per day. This dosage regimen may be adjusted to provide the optimum therapeutic response. For example, several divided doses may be administered daily or the dose may be proportionally reduced as indicated by the exigencies of the therapeutic situation. Preferred dosages are from about 15 ug to about 500 ug per kilogram of body weight per day. A decided practical advantage is that the active compound may be administered in a convenient manner such as by the oral, intravenous (where water soluble), intramuscular, intranasal, intraperitoneal, intradermal, suppository or intracerebroventricular routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 5 ug and 1000 mg of active compound.

The tablets, troches, pills, capsules and the like may also contain the following: A binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the injectable form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of surfactants. The preventions of the action of microorganisms can be brought about by various antibacterial and antifungal agents, for example, parabens, chlorobutanol, phenol, sorbic acid, thirmerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersions media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 ug to about 500 mg. Expressed in proportions the active compound is generally present in from about 0.5 ug/ml to about 500 mg/ml of carrier. In the case of compositions containing supplementary active ingredients, the dosages are determined by reference to the usual dose and manner of administration of the said ingredients.

In accordance with the subject invention as disclosed herein, exogenously administered CRF and stress result in identical changes in intestinal transit and similar changes in circulating adrenocorticotropic hormone (ACTH) levels. Furthermore, since CRF is likely to play an essential role in initiating both endocrine and autonomic responses to stress, it is probable, therefore, in accordance with the data disclosed herein, that CRF mediates the effects of stress on the gut. Accordingly, the ability of affecting the activity of CRF by, for example, blocking the CFR receptors, is examined relative to stress-induced disordered transit.

Alpha-helical CRF-(9-41) is a structurally constrained analog of CRF that retains little agonist activity but effectively antagonizes the effects of CRF and stress on pituitary ACTH release, both in vivo and in vitro (Rivier et al., 1984, *Science* 224:889-891). In accordance with the present invention, the CRF antagonist, alpha-helical CRF-(9-41), when administered intravenously or intracerebroventricularly, has no effect on small or large intestinal transit itself. However, as disclosed herein, alpha-helical CRF-(9-41) effectively antagonizes the effects of exogenous CRF on small and large intestinal transit when both compounds administered via the same route.

Consequently, to evaluate the importance of endogenous CRF in the response of the gut to stress, alpha-helical CRF-(9-41) is administered to a rat prior to the animal being stressed. The CRF antagonist significantly diminishes the stress-induced increases in colonic transit or fecal excretion.

Accordingly, as disclosed herein, blockade of endogenous CRF prevents the response of the colon to stress. In healthy subjects, stress is reported to increase the propulsive motor activity of the colon and cause diarrhea, without affecting the underlying characteristics of electrical activity. Patients with stress-related intestinal dysfunction (e.g. irritable bowel syndrome) have abnormal colonic motor activity - especially during times of stress. Antagonists to CRF, therefore, are contemplated herein to prevent the response of the colon to stress. Such antagonists, in accordance with the present invention are useful in inducing regression of functional bowel disease.

The following examples further illustrate the invention.

EXAMPLE 1

Materials and Methods

Animals

Female Sprague-Dawley rats (150-200 g) are used in all tests described herein. The animals are housed in groups of five in a temperature-controlled room on a 12 hour light-dark cycle (7:00 AM to 7:00 PM) and are allowed water and rat chow *ad libitum*. Animals are allowed at least one week to recover from shipping before experiments are performed.

Gastrointestinal Transit

Gastrointestinal transit, a measure of the propulsive motor activity of the intestine, is evaluated by the geometric center method (Miller et al., 1981, *J. Pharmacol. Methods* 6:211-217), in which a nonabsorable radioactive marker, $^{51}Cr$ (0.2 ml) as sodium chromate in distilled water, is instilled directly into the proximal duodenum and proximal colon via Silastic cannulas surgically implanted under Equithesin anesthesia 3-5 days earlier. Thirty-five minutes after administration of the chromium, the animals are killed, and the stomach and intestine are removed and counted for gamma radiation. Gastric emptying is evaluated by quantitating the percent radioactivity emptied from the stomach in a 15 minute period. Radiochromium in distilled water (0.2 ml) is administered by oral gavage, and the animals are killed and emptying assessed 15 minutes later. CRF or vehicle is administered intravenously or intracerebroventricularly immediately before $^{51}Cr$.

Wrapping-Restraint Stress

Wrapping-restraint stress, a relatively mild, nonulcerogenic model of restraint is used in all stress studies. Stressed animals are lightly anesthetized with ether, and their trunk, shoulders, and upper forelimbs are wrapped in a confining harness of masking tape. Control animals are lightly ether anesthetized but are not wrapped. Radiochromium is then administered, and the animals are killed 35 minutes later to assess intestinal transit. All stress experiments are performed in the late afternoon (4:00 to 7:00 PM) due to a strong circadian influence on the degree of intestinal dysfunction associated with stress at different times of the day.

Materials

CRF and alpha-helical CRF-(9-41) are purchased from Bachem. Drugs are diluted in distilled water, and NaOH (0.1 N) added to the solution, 1 ul at a time, until the compounds [CRF and alpha-helical CRF-(9-41)]go into solution, at a pH of ~6.8. The solutions are aliquotted into 25- and 50-ug supplies, lyophilized, and stored in a desiccator at 4°-8° C. until needed. Radioimmunoassay kits for determination of plasma levels of ACTH are purchased from ImmunoNuclear.

Statistics

Statistical analysis of the data is performed by one- or two-way analysis of variance followed by Neuman-Kuels test for comparison of means.

dose of CRF (0.3 ug i.c.v.). The results are shown in FIG. 2.

Restraint stress and CRF result in parallel changes in gastric emptying (FIG. 2A), small intestinal transit (FIG. 2B), large intestinal transit (FIG. 2C) and fecal pellet output. The response of the gut to stress and to CRF is identical both in direction and degree for this dose of CRF.

EXAMPLE 4

Endocrine Response to Exogenous and Endogenous CRF

The following example compares the endocrine response to a low dose of exogenous CRF (0.3 ug i.v.) and to stress-induced release of endogenous CRF by measuring plasma ACTH concentrations by radioimmunoassay in animals that are wrap restrained or treated with CRF. The results are shown in Table 1.

Blood is drawn from an indwelling jugular cannula, surgically placed under Equithesin anesthesia 3 days earlier. Blood (0.2 ml) is drawn 10 minutes before treatment, as well as 5, 10, 20, 30, 45, and 60 minutes after CRF administration or wrap-restraint stress. Blood is also drawn at the same time points from control animals are briefly ether anesthetized but which are not stressed or drug treated. The peak levels of ACTH induced by both wrap-restraint stress and CRF administration are very similar, although ACTH release in response to exogenous CRF follows a more rapid time course than stress-induced ACTH release.

TABLE 1

| | Plasma ACTH Concentrations After Administration of CRF (0.3 ug i.v.) or Wrap-Restraint Stress | | | | | | |
|---|---|---|---|---|---|---|---|
| | Plasma ACTH Concentration, pg/ml | | | | | | |
| GROUP | +10 | 5 | 10 | 20 | 30 | 45 | 60 |
| CRF | 64 ± 4 | 619 ± 70** | 494 ± 108* | 265 ± 93* | 174 ± 24 | 146 ± 33 | 141 ± 49 |
| Stress | 85 ± 45 | 787 ± 109** | 845 ± 155** | 765 ± 63** | 480 ± 66** | 255 ± 45* | 180 ± 10 |
| Control | 87 ± 14 | 310 ± 58* | 186 ± 31 | 167 ± 38 | 95 ± 14 | 155 ± 26 | 98 ± 28 |

Values are mean plasma adrenocorticotropic hormone (ACTH) concentrations ± SE at time (in minutes) indicated before and after corticotropin-releasing factor (CRF) administration or wrap-restraint stress; n = 3-4 animals/group.
*P < 0.05;
**P < 0.01 (ANOVA).

EXAMPLE 2

Effects of Exogenously Administered CRF

The following example examines the role of CRF in mediating the effects of stress on the gastrointestinal tract.

Figure 1B:
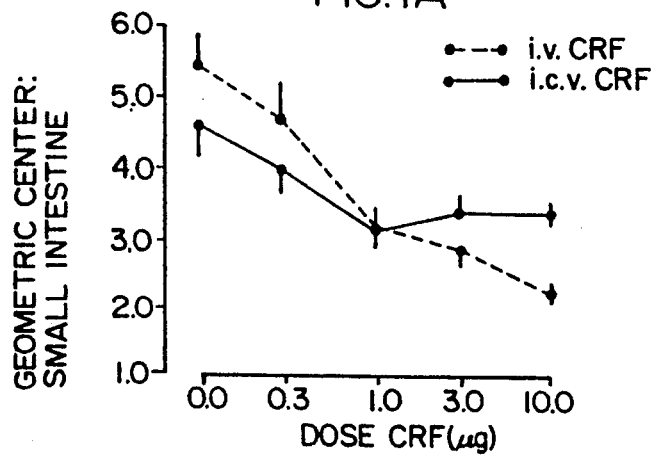
Figure 1C:
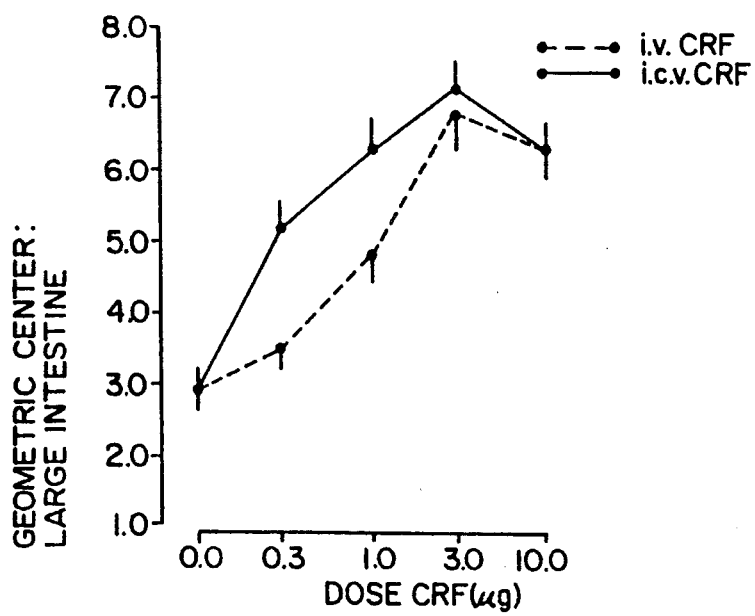

The results are shown in FIG. 1. CRF, administered intravenously (i.v.) or intracerebroventricularly (i.c.v.) results in a significant alteration in the propulsive activity of the gastrointestinal tract. Gastric emptying is inhibited in a dose-dependent manner, at doses ranging from 1.0 to 10.0 ug i.v. or i.c.v. (FIG. 1A). In addition, CRF (0.3 to 10.0 ug) like stress, inhibits small intestinal transit (FIG. 1B) and increases colonic transit (FIG. 1C), resulting in increased fecal pellet output, and at higher doses, diarrhea. Intravenously administered CRF and intracerebroventricularly administered CRF are equally effective.

EXAMPLE 3

Comparison of Acute Wrap-Restraint Stress and Lowest Effective Dose of CRF

This example compares the gastric and intestinal effects associated with restraint stress to those resulting from exogenous administration of the lowest effective

EXAMPLE 5

Effect of Alpha-Helical CRF-(9-41) on Action of Endogenous CRF

The foregoing Examples show that exogenously administered CRF and stress result in identical changes in intestinal transit and similar changes in circulating ACTH levels. Since CRF is likely to play an essential role in initiating both endocrine and autonomic responses to stress, it is probable that CRF mediates the effects of stress on the gut and that blockade of CRF receptors would lessen stress-induced disordered transit. Alpha-Helical CRF-(9-41) is a structurally constrained analog of CRF that retains little agonist activity but effectively antagonizes the effects of CRF and stress on pituitary ACTH release, both in vivo and in vitro. The antagonist, alpha-helical CRF-(4-41) (50 ug, i.v. or i.c.v.), has no effect on small or larger intestinal transit itself when administered into the brain or the bloodstream. However, alpha-helical CRF-(4-41) (50 ug i.v. or i.c.v.) effectively antagonizes the effects of exogenous CRF (3 and 10 ug i.v. or i.c.v.) on small and large intestinal transit when both compounds are administered via the same route.

Figure 3A:
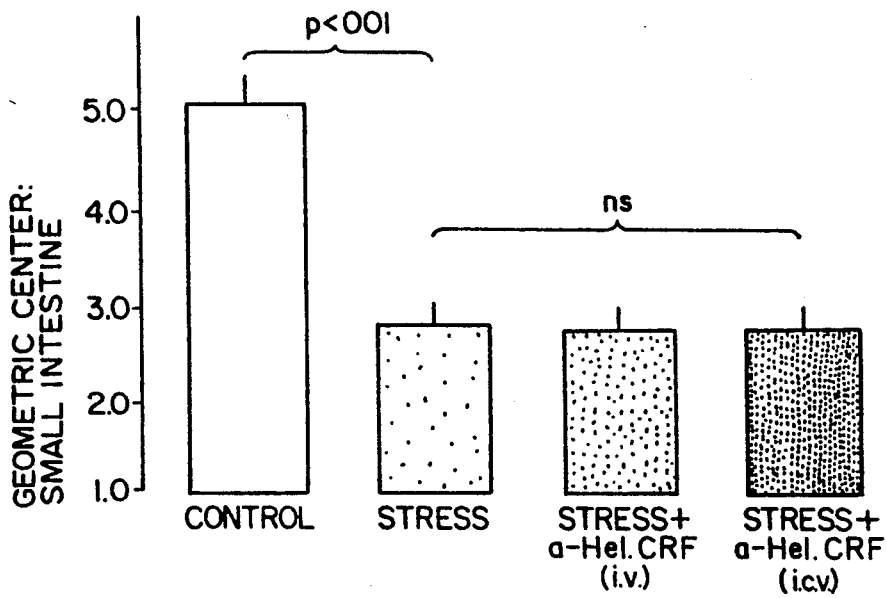
FIG. 3 is a bar diagram showing the effects of alpha-helical CRF-(9-41) on stress-induced intestinal dysfunction. The data represent (A) small intestinal transit; (B) large intestinal transit; and (C) fecal excrement.
Figure 3B:
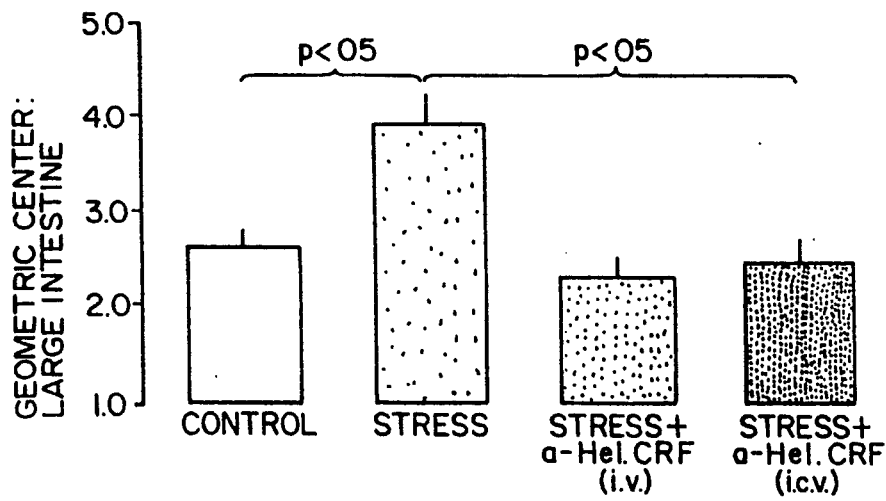
Figure 3C:
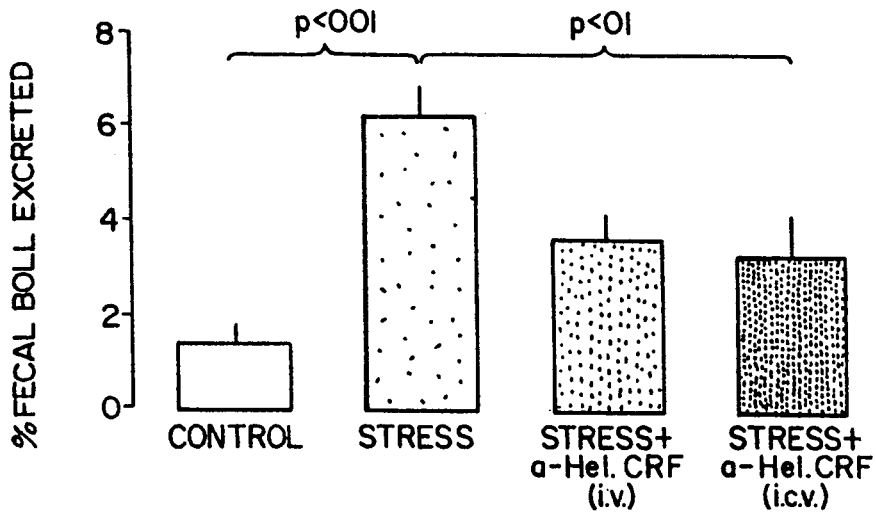

To evaluate the importance of endogenous CRF in the response of the gut to stress, alpha-helical CRF-(4-41) (50 ug) is administered into a lateral cerebral ventricle or into the bloodstream via the tail vein immediately before the animals are stressed. FIG. 3 shows the results of alpha-helical CRF-(9-41) pretreatment on stress-induced gastrointestinal dysfunction. The antagonist did not affect stress-induced inhibition of small intestinal transit (FIG. 3A). However, the antagonist completely blocked the stress-induced increase in large intestinal transit (3B) and significantly diminished the stress-induced increase in fecal pellet output (FIG. 3C). A higher dose of the antagonist (100 $\mu$g i.c.v.) administered to a group of animals exposed to stress; however, the higher dose did not result in a further decrease in stress-induced increases in colonic transit or fecal excretion. Even at this high dose, alpha-helical CRF-(9-41) did not affect stress-induced inhibition of small intestinal transit.

What is claimed is:

1. A method of inducing regression of functional bowel disease in a mammal comprising the administration to said mammal of an effective amount of an antagonist to corticotropin-releasing factor (CRF).

2. The method according to claim 1 wherein the mammal is a human.

3. The method according to claim 1 wherein the regression is effected by oral, intravenous, intramuscular, intranasal, intradermal, intraperitoneal, suppository or intracerebroventricular administration.

4. The method according to claim 1 wherein the antagonist is alpha-helical CRF-(9-41).

5. The method according to claim 1 wherein the effective amount is from about 0.5 $\mu$g to about 500 mg of said antagonist per kilogram of body weight per day.

* * * * *

UNITED STATES PATENT AND TRADEMARK OFFICE
CERTIFICATE OF CORRECTION

PATENT NO. : 5,236,901
DATED : August 17, 1993
INVENTOR(S) : Thomas F. Burks, et al.

It is certified that error appears in the above-indentified patent and that said Letters Patent is hereby corrected as shown below:

Column 6, line 14: after "compounds" insert --are--

Column 8, line 25: after "animals" insert --that--

Column 8, line 35: "+10" should read -- -10--

Column 8, lines 61 & 64: "(4-41)" should read --(9-41)--

Column 9, lines 2-3: "(4-41)" should read --(9-41)--

Signed and Sealed this

Fourteenth Day of June, 1994

Attest:

BRUCE LEHMAN

*Attesting Officer*     *Commissioner of Patents and Trademarks*